US00RE33980E

United States Patent [19]

Matsuura et al.

[11] E Patent Number: Re. 33,980

[45] Reissued Date of Patent: Jun. 30, 1992

[54] THICK-FILM GAS-SENSITIVE ELEMENT

[75] Inventors: Toshitaka Matsuura; Teppei Okawa; Keizo Furusaki; Akio Takami, all of Nagoya, Japan

[73] Assignee: NGK Spark Plug Co., Ltd., Nagoya, Japan

[21] Appl. No.: 517,749

[22] Filed: May 2, 1990

Related U.S. Patent Documents

Reissue of:

[64] Patent No.: 4,857,275
Issued: Aug. 15, 1989
Appl. No.: 27,357
Filed: Mar. 18, 1987

[30] Foreign Application Priority Data

Mar. 19, 1986 [JP] Japan ..... 61-172
Mar. 19, 1986 [JP] Japan ..... 61-173
Mar. 19, 1986 [JP] Japan ..... 61-174

[51] Int. Cl.[5] ..... G01N 27/22

[52] U.S. Cl. ..... 422/98; 73/23.32; 338/34; 422/94; 422/95; 422/96; 422/97; 424/343; 424/344; 436/152

[58] Field of Search ..... 422/94, 95, 96, 97, 422/98; 427/343, 344; 436/152; 73/27 R; 338/34

[56] References Cited

U.S. PATENT DOCUMENTS

| | | | |
|---|---|---|---|
| 3,092,799 | 6/1963 | Baker | 422/95 |
| 3,901,067 | 8/1975 | Boardman, Jr. et al. | 422/98 |
| 4,072,467 | 2/1978 | Jones | 422/97 |
| 4,242,303 | 12/1980 | Takahashi et al. | 422/98 |
| 4,253,302 | 3/1981 | Asano et al. | 60/276 |
| 4,255,559 | 3/1981 | Achari et al. | 422/98 |
| 4,259,292 | 3/1981 | Ichinose et al. | 422/98 |
| 4,303,612 | 12/1981 | Sonley | 422/97 |
| 4,453,397 | 6/1984 | Ohta et al. | 338/34 |
| 4,500,412 | 2/1985 | Takahashi et al. | 204/425 |
| 4,652,849 | 3/1987 | Matsuura et al. | 422/98 |

FOREIGN PATENT DOCUMENTS

| | | | |
|---|---|---|---|
| 0014091 | 8/1980 | European Pat. Off. . | |
| 0102067 | 3/1984 | European Pat. Off. . | |
| 0141090 | 5/1985 | European Pat. Off. . | |
| 2908916 | 9/1980 | Fed. Rep. of Germany . | |
| 3313752 | 10/1983 | Fed. Rep. of Germany . | |
| 3515035 | 11/1985 | Fed. Rep. of Germany | 422/98 |
| 60-158346 | 8/1985 | Japan . | |

*Primary Examiner*—Robert J. Warden
*Assistant Examiner*—Timothy M. McMahon
*Attorney, Agent, or Firm*—Fleit, Jacobson, Cohn, Price, Holman & Stern

[57] ABSTRACT

A laminar gas-sensitive thick film consisting of ceramic semiconductor and metallic catalyzer is formed across a pair of electrodes carried by a ceramic substrate, and the nature of metallic catalyzer on an outer surface layer of the thick film is different from that of metallic catalyzer in that portion of the thick film which is in the proximity of the electrodes.

10 Claims, 7 Drawing Sheets

THICK-FILM GAS-SENSITIVE ELEMENT

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a thick-film gas-sensitive element which is suitable for a gas sensor such as an oxygen sensor, and more particularly the invention relates to a thick-film gas-sensitive element having a high resistivity against variation of its operating characteristics due to deterioration of metallic catalyzer on its outer surface layer. The variation in operating characteristics of an oxygen sensor has been a cause of instability of automobile exhaust gas cleaning system, for instance, an instability in that a controlled air-fuel-ratio point in a feedback control system for cleaning engine exhaust gas with ternary catalyzer is shifted to lean side after its durability test.

2. Related Art Statement

The invention disclosed, in their Japanese Patent Laying-open Specification No. 158346/1985, a titania thick-film gas-sensitive element with 5–30 mole % of platinum-group metallic catalyzer particles dispersed therein. Ensuing studies have shown that the metallic catalyzer in the outer surface layer of the thick film is responsible for certain changes in its performance as a gas-sensitive element. More specifically, when the titania thick-film gas-sensitive element is used in a feedback control system for cleaning automobile exhaust gas with ternary catalyzer, controlled air-fuel-ratio point of the control system has been shifted to lean side after its durability test, and the cause of such shift has been found to be deterioration of the metallic catalyzer particles in the outer surface layer of the thick film.

Various improvements of durability of gas-sensitive thick films have been disclosed in Japanese Patent Laying-open Specifications such as No. 11226/1978,
No. 130093/1978,
No. 48596/1979, and
No. 106147/1981.

In particular, the last-mentioned Specification taught durability improvement of a pellet type gas-sensitive element by reducing the amount of catalyzer in its outer surface layer as compared with that in its inner portion across electrodes. Although the disclosed improvement contributes to suppression of the above mentioned shift of the controlled air-fuel-ratio point, it does not prevent the troublesome deterioration of the catalyzer particles in the outer surface layer during use. Besides, the reduction of the amount of catalyzer particles is clearly undesirable from the standpoint of the function of trapping poisonous substances, such as lead (Pb) and phosphorus (P), for the purpose of preventing the poisonous substances in exhaust gas from entering into the gas-sensitive element.

As result of a series of studies on the thick-film gas-sensitive element of the above-mentioned Japanese Patent Laying-open Specification No. 158346/1985, the inventors have found that a change in the emission characteristics of the thick film occurs during durability test due to change in the nature or structure of the metallic catalyzer and that such change of the catalyzer mainly depends on adsorption of specific components of the exhaust gas being sensed. The inventors noted a possibility of improvement in the durability of the thick-film gas-sensitive element by minimizing influence of the ambient gas.

SUMMARY OF THE INVENTION

Therefore, an object of the invention is to solve the problem of the above-mentioned shift in the operating characteristics by providing an improved thick-film gas-sensitive element of laminate structure.

A thick-film gas-sensitive element according to the present invention comprises a ceramic substrate carrying a pair of electrodes disposed thereon and a gas-sensitive thick film deposited on said ceramic substrate so as to extend across the pair of electrodes. The gas-sensitive thick film consists of ceramic semiconductor and metallic catalyzer, and the thick film has a laminate structure. An outer surface layer of the gas-sensitive thick film away from the substrate contains different metallic catalyzer than that in an inner portion of the gas-sensitive thick film in proximity of the electrodes.

In a preferred embodiment of the thick-film gas-sensitive catalyzer in the outer surface layer contains less than 0.2 mole % of rhodium (Rh) based on amount of the ceramic semiconductor therein, while the metallic catalyzer in the inner portion contains 0.2–3 mole % of rhodium (Rh) on a similar basis.

Another embodiment of the invention uses metallic catalyzer with a larger grain size in the outer surface layer than that of metallic catalyzer in the inner portion on the side of the electrodes. Similarly, the grain size of ceramic semiconductor in the outer surface layer can be larger than that of ceramic semiconductor in the inner portion in the proximity of the electrodes.

The metallic catalyzer in the outer surface layer of the gas-sensitive thick film can be platinum (Pt) particles with a grain size of larger than 0.5 μm, while the metallic catalyzer in the inner portion of the gas-sensitive thick film can be particles of rhodium (Rh) or its compound with a grain size of less than 0.5 μm in the amount of 0.2–3 mole % based on amount of ceramic semiconductor therein.

The laminate structure of the gas-sensitive thick film can be formed by firing layers of ceramic semiconductor paste, while providing different dispersions of metallic catalyzer in different layers by impregnation of different solution of salt of metallic catalyzer in the fired paste layers followed by thermal cracking of the salt.

In a different embodiment of the invention, the laminate structure of the gas-sensitive thick film is formed of fire paste layers of ceramic semiconductor, while providing different dispersions of metallic catalyzer in different layers by different mixing of metallic catalyzer particles in different ceramic semiconductor pastes followed by laminate spreading and firing of the ceramic semiconductor pastes.

Further, the laminate structure of the gas-sensitive thick film can be formed of fired paste layers of ceramic semiconductor with differently dispersed metallic catalyzer. Namely, it can be formed by using at least one layer having a dispersion of metallic catalyzer produced by impregnation of solution of salt of the metallic catalyzer in the fired paste layer followed by thermal cracking of the salt, along with at least one other layer having a different dispersion of metallic catalyzer produced by mixing of particles of the metallic catalyzer in ceramic semiconductor paste followed by laminate spreading and firing of the ceramic semiconductor paste.

The ceramic substrate to be used in the thick-film gas-sensitive element can be a regularly used ceramic substrate. For instance, it can be a sintered ceramic substrate in the form of a thin film which mainly consists of alumina, beryllia, mullite, steatite, or the like.

The electrodes can be made of electrically conductive material which withstands the sintering temperature of the ceramic substrate. Conductors mainly consisting of gold or platinum group elements are commonly used, and platinum is particularly suitable for the electrodes in the gas-sensitive thick film of the invention, because platinum can be also used as conductors for making electric connections to the electrodes.

The gas-sensitive thick film can be made by using a ceramic semiconductor consisting of a metal oxide such as tin oxide ($SnO_2$), titania ($TiO_2$), cobalt oxide (CoO), zinc oxide (ZnO), niobium oxide ($Nb_2O_5$), chromium oxide ($Cr_2O_3$), and the like. From the standpoint of heat resistance, tin oxide and titania are preferable, and the use of titania is most preferable.

The gas-sensitive thick film preferably contains 0.2–3 mole % of platinum group metal, and its preferable thickness is 100–500 μm.

As to the catalyzer in the gas-sensitive thick film, very widely used platinum provides excellent gas sensitivity. However, when used in hot exhaust gas over a long period of time, platinum tends to evaporate and reduce its durability.

When rhodium (Rh), rhodium-platinum (Rh-Pt) alloy, or rhodium-palladium (Rh-Pd) alloy is used in lieu of platinum, the durability is noticeably improved by the high heat resistivity of rhodium.

However, if rhodium is dispersed throughout the gas-sensitive thick film, since rhodium is easily oxidized in an oxidizing atmosphere, the nature of rhodium tends to vary when exposed to certain atmosphere over a long period of time. For instance, a change in the oxidation-reduction speed of rhodium may affect the response of the gas-sensitive element to such an extent that the control point of an exhaust gas control system using the gas-sensitive element may be shifted thereby.

The inventors found that the gas sensitivity of a thick-film gas-sensitive element is ruled by the conditions in the proximity of electrodes but not by the conditions of the outer surface of the thick film. Based on such finding, the inventors have succeeded in producing a gas-sensitive element with high heat resistivity and a high durability by making a thick film of laminate structure in which a high rhodium concentration is provided only in the proximity of the electrodes. With such laminate structure, the instability of rhodium depending on the atmosphere is minimized. More specifically, the rhodium concentration on the outer surface of the thick film is preferably less than 0.2 mole %, and if it is higher than 0.2 mole %, the dependency of the gas-sensitive element characteristics on the atmosphere increases and the response of the gas-sensitive element is reduced.

On the other hand, the preferable range of rhodium concentration in a layer in the proximity of the electrodes is 0.2–3 mole %. If it is less than 0.2 mole %, the durability for use at a high temperature becomes insufficient, while if it is more than 3 mole %, the response of the gas-sensitive element becomes inferior Besides rhodium, the commonly used catalyzer such as platinum and/or palladium may be used as auxiliary catalyzer in the form of metallic element or alloy with rhodium. Total amount of the metallic catalyzer should be less than 30 mole %, because the metallic catalyzer in excess of such limit tends to reduce the response of the gas-sensitive element.

The thickness of the layer in the proximity of the electrodes and the thickness of the outer surface layer can be determined depending on the actual conditions of specific application. From the standpoint of the stability of controlled air-fuel-ratio in durability test and the stability of gas sensitivity, the thickness of each layer should not be less than 50 μm respectively. The total thickness of the thick film should be 100–500 μm, because the thickness less than 100 μm results in an insufficient durability while the thickness in excess of 500 μm reduces the response of the gas-sensitive element and tends to cause peeling off of the thick film from the substrate due to difference in their thermal expansion under certain operating conditions.

The catalyzer in the outer surface layer acts to trap poisonous substances in the exhaust gas. Accordingly, for applications which are possibly exposed to poisonous substances, addition of a certain amount of platinum into the outer surface layer is preferable. If the platinum in the outer surface layer changes its nature during the use, the gas sensitivity of the thick film is affected thereby and the controlled point for cleaning the exhaust gas is detrimentally shifted to the lean side (i.e., the dilute side). The inventors found that such change of platinum in the outer surface layer can be prevented by using platinum catalyzer of larger grain size in the outer surface layer than that in the inner layer in the proximity of the electrodes. The grain size of the majority of the platinum particles in the outer surface layer should be larger than 0.5 μm. The platinum particles smaller than 0.5 μm are easily evaporated during the use, and the gas sensitivity of the thick film is changed thereby.

The use of platinum particles with a grain size of larger than 0.5 μm results in an initial gas sensitivity which corresponds to the above-mentioned gas sensitivity after the use, so that with such larger platinum particles in the outer surface layer the gas sensitivity hardly changes during the use and the performance of the gas-sensitive element is stabilized.

More particularly, the ceramic particles to be used in the outer surface layer of the thick film of the invention are preferably calcined at 1,200°–1,300° C., so as to make the grain size of the particles 1–5 μm. Thus, change in nature or structure of such particles after the durability test is prevented. If the calcining temperature is higher than 1,300° C., the gas-sensitivity of the ceramic particles is reduced and the catalytic function of the metallic catalyzer is greatly reduced due to excessive growth of the catalyzer particles. Since the thick-film gas-sensitive element will be used at a temperature of up to 1,000° C., the calcining temperature should be reasonably higher than this operating temperature, and the minimum calcining temperature of 1,200° C. is selected. When calcined at a temperature higher than 1,200° C., the average grain size of the metallic catalyzer in the ceramic particles is made larger than 0.5 μm.

On the other hand, the ceramic particles in the inner layer in the proximity of the electrodes are calcined at a temperature lower than 1,200° C., and grain size of 0.5–3 μm is provided for the ceramic particles so as to produce satisfactory gas-sensitivity and ensure a high stability of such gas-sensitivity.

Two methods are available for adding the metallic catalyzer in the ceramic thick film; namely, a method of adding particles of the metallic catalyzer and a method of impregnating a solution of salt of the metallic catalyzer followed by thermal cracking of the salt so as to precipitate the catalyzer metal. To obtain a high gas-sensitivity at the inner layer in the proximity of the electrodes, small grain size is preferable for the metallic catalyzer therein. To this end, the impregnating method is suitable.

Reaction of the thermal cracking can be effected by a burner or in an electric furnace. Since the invention requires satisfactory precipitation in the proximity of the electrodes, thermal cracking in a reducing furnace is preferable.

For production of metallic catalyzer with fine grain size in the proximity of the electrodes, the method of adding separately pulverized small particles is possible but not practical due to difficulty in obtaining uniform dispersion and stable operating characteristics. Thus, the impregnation method is preferable. More specifically, a ceramic semiconductor layer is spread on a ceramic substrate and baked, and a solution of a salt of the metallic catalyzer, which salt produces the metallic catalyzer upon thermal cracking, is impregnated in the thus baked layer of the ceramic semiconductor, and then the impregnated solution is thermally cracked at a comparatively low temperature.

The coarse particles of metallic catalyzer, on the other hand, can be easily produced by the method of adding particles, and this method is preferable. However, the impregnation method can be used in this case too. It is noted here that the grain size of the metallic catalyzer to be produced by thermal cracking can be controlled by regulating the temperature of the thermal cracking reaction. The thick-film gas-sensitive element according to the present invention can be produced by a suitable combination of the impregnation method and the particle adding method while considering their respective advantages.

Generally speaking, satisfactory gas sensitivity of the thick-film gas-sensitive element is available only when its temperature is high. Accordingly, if it is intended to use the gas-sensitive element at a low ambient temperature, heating by a suitable heater may be necessary for warming up the element. From the standpoint of miniaturization and productivity, it is preferable to form a heater layer on the ceramic substrate along with the gas-sensitive thick film. The heater layer should be such that the gas-sensitive thick film is never heated above 500° C. lest the corrosion resistivity of the gas-sensitive element be deteriorated.

BRIEF DESCRIPTION OF THE DRAWINGS

For better understanding of the invention, reference is made to the accompanying drawings, in which.

Figure 1:
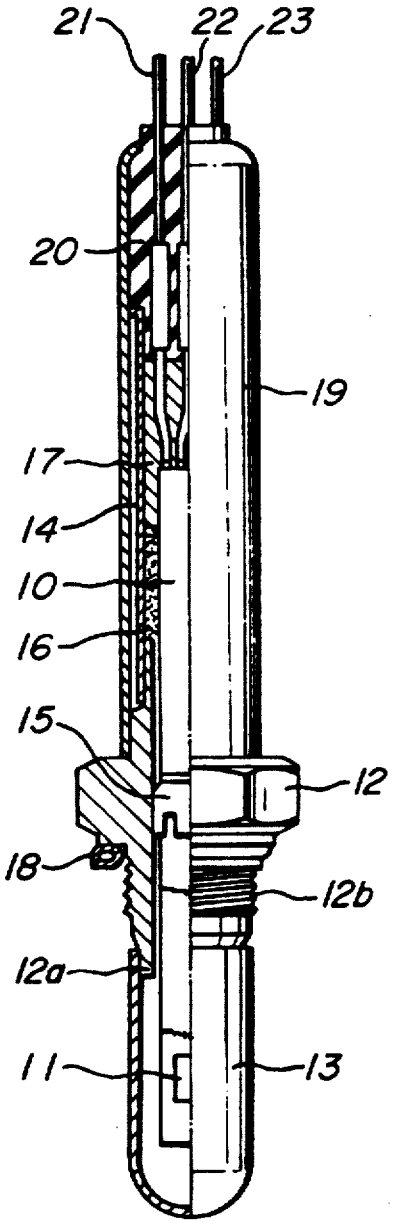
FIG. 1 is a partially cutaway overall side view of an oxygen detector having an oxygen sensor embodying the present invention mounted thereon.

Throughout different views of the drawing, 10 is a gas sensor, 11 is a gas-sensitive element, 12 is a body hardware, 13 is a protector, 14 is an inner cylinder, 15 is a spacer, 16 is filler powder, 17 is a glass seal, 18 is a gasket, 19 is an outer cylinder, 20 is a seal, 21 through 23 are lead wires, 24 through 26 are compressible connectors, 31 through 33 are terminals, 40 is a ceramic substrate, 41 is a ceramic cover layer, 42 and 43 are electrodes, 44 is a heater layer, 45 through 47 are end portions, 48 through 50 are platinum lead wires, 51 is an opening, 52 represents granulated spherical ceramic particles, 60 is a test engine, 61a is a sensor-mounting portion, 65 is a control unit, 67 is a ternary catalyzer unit, 70 is a power source, 72 is a heater, 74 is a resistance representing a gas-sensitive element, and 76 is a comparison resistance.

DESCRIPTION OF THE PREFERRED EMBODIMENT

The construction of a thick-film gas-sensitive element of the invention will now be described in detail by referring to an embodiment which is an oxygen sensor for detecting oxygen concentration in exhaust gas from an internal combustion engine.

In FIG. 1, showing a partially cutaway overall side view of an oxygen sensor, a gas sensor 10 has a gas-sensitive element 11 as an embodiment of the invention formed on a ceramic substrate. The gas-sensitive element 11 is formed of a gas-sensitive thick film covering a pair of electrodes disposed on the ceramic substrate. A cylindrical body hardware 12 houses the gas sensor 10 therein and is mountable on an internal combustion engine. A protector 13 is coupled to the engine-side end 12a of the body hardware 12, so as to protect the gas sensor 10. The gas sensor 10 is held by an inner cylinder 14 with a spacer 15 inserted therebetween, which inner cylinder 14 is carried by the body hardware 12.

Filler powder 16 and glass seal 17 are stuffed between the gas sensor 10 and the inner cylinder 14 so as to keep the gas sensor 10 in position.

To facilitate the mounting of the oxygen detector to an engine, the body hardware 12 has a threaded portion 12b. Thus, the oxygen detector can be screwed to the engine with a gasket 18 disposed between the body hardware 12 and the screwed portion of the engine wall, so as to prevent engine exhaust gas from leaking through the screwed portion.

The filler powder 16, which is preferably a powder mixture of talc and glass at a ratio of 1:1, acts to fix the gas sensor 10 in position within the inner cylinder 14. The glass seal 17 stuffed in the inner cylinder 14, which is preferably made of glass with a low melting point, acts to prevent the gas being sensed from leaking and to protect terminals of the gas sensor 10. To this end, the glass seal 17 covers and holds both a part of the gas sensor 10 and joints of the terminals with platinum lead wires to be described hereinafter.

Figure 2:
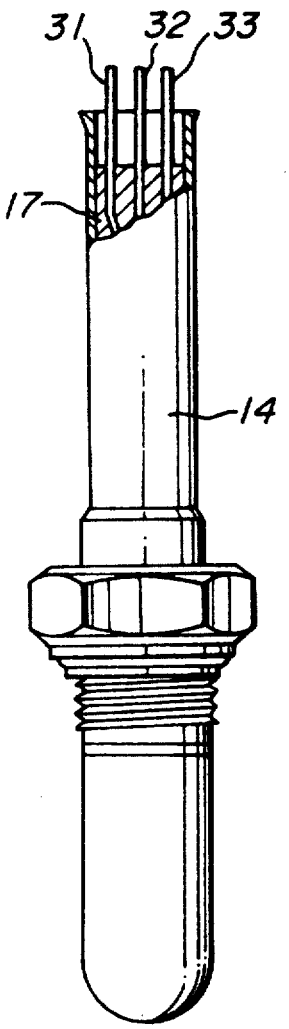
FIG. 2 is a partially cutaway side view of an inner cylinder of the oxygen detector, showing terminals extending outward from glass seal of the inner cylinder.
Figure 3:
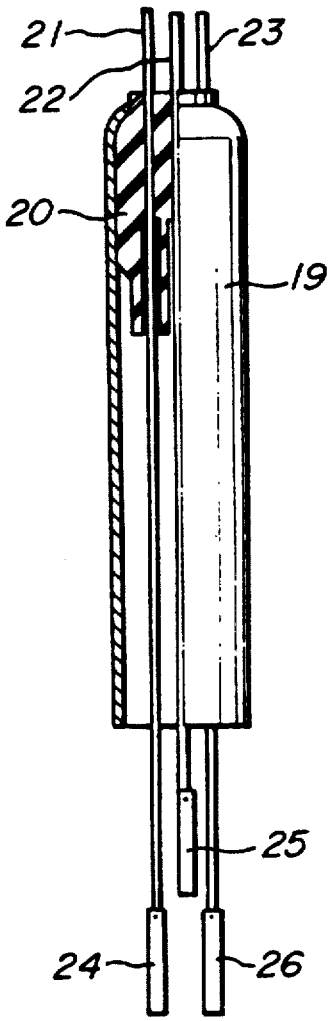
FIG. 3 is a partially cutaway side view of an outer cylinder of the oxygen detector, showing the manner in which one end of the outer cylinder is closed by a sealing before it is coupled with the inner cylinder.

An outer cylinder 19 is coupled to the body hardware 12 so as to cover the inner cylinder 14. A sealing 20 made of silicone rubber is stuffed between the inner cylinder 14 and the outer cylinder 19, so as to protect and insulate both outgoing lead wires 21 through 23 and their joints with the terminals 31 through 33 of the gas sensor 10 projecting from the glass seal 17 as shown in FIG. 2. To facilitate the joining of the lead wires 21 through 23 with the terminals 31 through 33, the sealing 20 and the lead wires 21 through 23 may be placed in the inside of the outer cylinder 19 beforehand, and compressible connectors 24 through 26 may be joined to the inner end of the lead wires 21 through 23 respectively, as shown in FIG. 3. Thus, the terminals 31 through 33 of the gas sensor 10 may be joined to the outer ends of the connectors 24 through 26 respectively.

Samples of the gas sensor 10 were prepared by a process as shown in the plan views of FIG. 4A through FIG. 8A. FIG. 4B through FIG. 8B show sections taken along the lines with arrows B in FIG. 4A through FIG. 8A respectively.

Green sheets for ceramic substrates 40 and ceramic cover layers 41 were formed in the following manner: Namely, 100 parts by weight of powder mixture were prepared by mixing 92% by weight (wt %) of alumina ($Al_2O_3$) with a mean diameter of 1.5 μm, 4 wt % of silica ($SiO_2$), 2 wt % of calcia ($CaO_2$) and 2 wt % of magnesia (MgO); 12 parts by weight of butyral resin and 6 parts by weight of dibutyl phthalate (DBP) were added to the 100 parts by weight of the powder mixture; a slurry was made by mixing the powder mixture in an organic solvent; and the green sheets were formed from the slurry by using a doctor blade. The green sheet for the ceramic substrate 40 was 1 mm thick, while the green sheet for the cover ceramic layer 41 was 0.3 mm thick.

Layers for electrodes 42, 43 and a heater layer 44 were printed in the form of thick film patterns, by using a platinum plate made by adding 7% of alumina ($Al_2O_3$) based on the amount of platinum. The electrodes 42 and 43 are for measuring the electric resistance of the above-mentioned gas-sensitive element 11, and the heater layer 44 is for heating the gas-sensitive element 11. End portions 45 through 47 are for applying an electric current to the heater layer 44 and extracting the output signal from the gas-sensitive element 11.

Figure 4A:
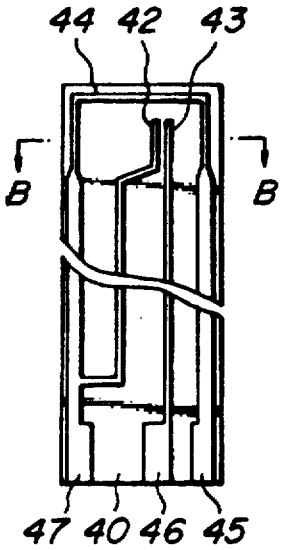
FIG. 4A, FIG. 5A, FIG. 6A, FIG. 7A and FIG. 8A are schematic plan views, showing different steps of the process in which a gas-sensitive element of the invention is assembled.
Figure 5A:
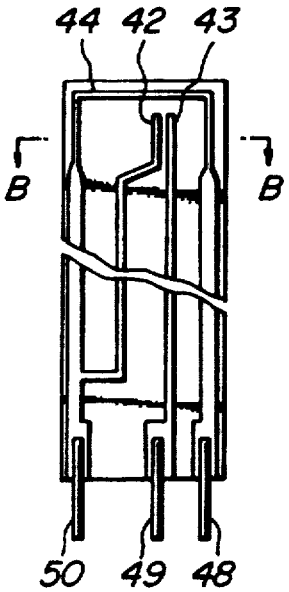
Figure 4B:
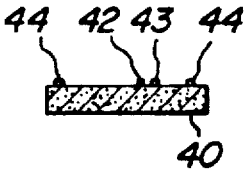
FIG. 4B, FIG. 5B, FIG. 6B, FIG. 7B and FIG. 8B are sectional views taken along the line with arrows B in FIG. 4A, FIG. 5A, FIG. 6A, FIG. 7A and FIG. 8A, respectively.
Figure 5B:
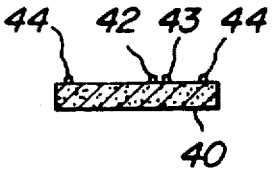

To prepare the gas sensor 10, patterns for the electrodes 42, 43 and the heater layer 44 were at first printed in thick films on the green sheet for the ceramic substrate 40 together with their end portions 45 through 47 by using the platinum paste, as shown in FIG. 4A and FIG. 4B. Thereafter, platinum lead wires 48 through 50 with a diameter of 0.2 mm were disposed on the end portions 45 through 47 of the patterns respectively, as shown in FIG. 5A. It was a matter of course that, in printing the thick film of the heater layer 44, its patterned width was so adjusted as to ensure proper heating of the gas-sensitive element 11 upon application of a predetermined voltage thereacross.

Figure 6A:
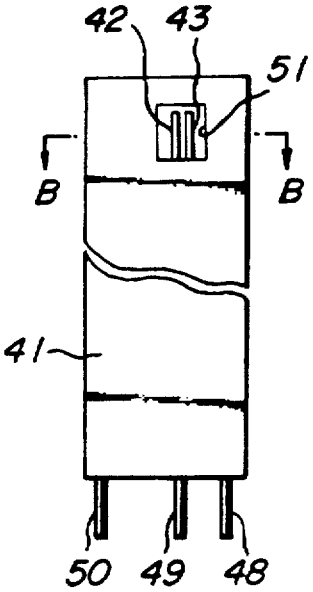

As shown in FIG. 6A, an opening 51 was bored, for instance by punching, through the green sheet for the cover ceramic layer 41 at such a position that, when the thus bored green sheet was overlaid on the green sheet for the ceramic substrate 40 so as to cover the entire pattern-printed surface of the latter sheet, the tip portions of the electrodes 42 and 43 were exposed to the outside through the opening 51. After being overlaid in the above manner, the green sheet for the cover ceramic layer 41 was joined to the green sheet for the ceramic substrate 40 by heating and pressing.

Thus, the printed patterns for the electrodes 42, 43 and the heater layer 44 were sandwiched between the green sheets for the ceramic substrate 40 and the cover ceramic layer 41, with the platinum lead wires 48 through 50 partially projecting to the outside of the thus joined green sheets and the tip portions of the electrodes 42 and 43 being exposed to the outside through the opening 51.

Figure 6B:
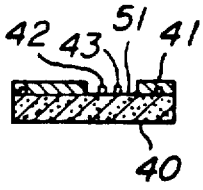
Figure 6C:
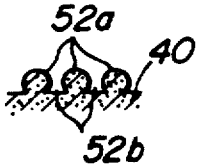
FIG. 6C is a fractional sectional view, showing granulated ceramic particles integrally bonded to a ceramic substrate so as to provide a roughened surface thereon.

Granulated spherical ceramic particles (secondary particles) 52 with a grain size of 80–150 mesh, made of the same material as that of the above green sheets, were scattered through the opening 51 onto the exposed portion of the green sheet for the ceramic substrate 40 so as to be dispersed thereon in a single-particle layer. The green sheets with the ceramic particles 52 thus scattered thereon were heated in air at 1,500° C. for 2 hours. Whereby, the ceramic particles 52 were bonded to that surface portion of the ceramic substrate 40 which faced the opening 51 of the cover ceramic layer 41, as shown in FIG. 6C, so that such surface portion was roughened.

The thus bonded ceramic particles 52 formed projections 52a on the ceramic substrate 40 while defining recesses 52b therebetween. The cross-sectional area of the recess 52b in parallel to the plane of the ceramic substrate 40 increased with the depth thereof. Accordingly, when a thick film of gas-sensitive metal oxide paste was applied thereon as described hereinafter, bottom portion of such thick film intruded into such recesses 52b and the thick film was firmly bonded to the ceramic substrate 40, especially after being fired.

Figure 7A:
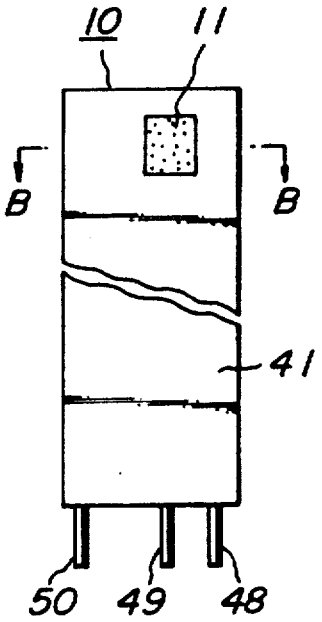
Figure 7B:
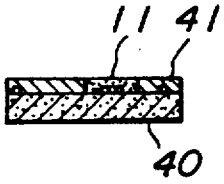

A gas-sensitive element 11 was overlaid on the opening 51 of the ceramic cover layer 41, as shown in FIG. 7A and FIG. 7B. Steps for the process for over the gas-sensitive element 11 were as follows.

(1) Preparation of paste for titania layer (I):

Powder material for the inner titania ($TiO_2$) layer (I) was prepared by calcining 500 g of starting titania powder in air at 1,200° C. for one hour. A paste was made by mixing 100 g of BUTYL CARBITOL (a merchandise mark of 2-(2-butoxy ethoxy)ethanol) with 100 g of the above-mentioned powder material, crashing and mixing the mixture in a ball mill for 24 hours, adding 2 g of butyral as a binder into 100 g of titania, and kneading the binder-added mixture for one hour.

(2) Formation of a titania layer (I):

The inner titania layer (I) was formed by spreading the paste, which was prepared in the above step (1), in the window 51 of the ceramic cover layer 41, drying the spread layer and baking the dried layer at 1,100° C. for two hours.

(3) Distribution of metallic catalyzer (I):

A solution of salt of metallic catalyzer (I) was impregnated in the titania layer (I) which was formed in the above step (2). The kind and concentration of the salt in the solution were determined depending on the type and the amount of desired metallic catalyzer. For instance, in the case of distributing 5 mole % of platinum (Pt) and 0.5 mole % of rhodium (Rh), 1 μl of an aqueous solution of chloroplatinic acid and rhodic acid containing platinum at a rate of 200 g/l and rhodium at a rate of 20 g/l was impregnated per 100 μm of the titania layer thickness.

The thus impregnated titania layer was dried at 100°-150° C. for one hour. Thermal cracking of the salt was carried out by heating in an electric furnace at 800° C., so as to produce platinum particles with a grain size of about 0.1 μm in the titania layer.

The formation of the inner layer in the proximity of the electrodes was completed by the foregoing steps.

(4) Preparation of paste for titania layer (II):

To produce different metallic catalyzer in an outer titania layer (II) as compared with that in the above-mentioned titania layer (I) by the particle-addition method, more specifically to produce 10 mole % of platinum, 10 mole % of platinum black with a grain size of 1.2 μm was added to the starting titania ($TiO_2$) powder.

Separately, in order to produce the same titania layer (II) as mentioned above by the impregnation method, an aqueous solution of chloroplatinic acid was impregnated in the starting titania ($TiO_2$) powder at a rate of 10 mole % in terms of platinum, drying the impregnated powder at 200°-250° C. for 24 hours, baking the dried powder in an electric furnace at 1,200° C. for one hour so as to precipitate platinum particles with a grain size of 1.3 μm in the titania powder.

A paste for the titania layer (II) of the particle-addition method was made by mixing 100 g of BUTYL CARBITOL with 100 g of the above-mentioned platinum-black-added powder material, crashing and mixing the mixture in a ball mill for 24 hours, adding 2 g of butyral as a binder into 100 g of titania, and kneading the binder-added mixture for one hour.

Separately, a paste for the titania layer (II) of the impregnation method was made by mixing 100 g of BUTYL CARBITOL with 100 g of the above-mentioned impregnated powder material, crashing and mixing the mixture in a ball mill for 24 hours, adding 2 g of butyral as a binder into 100 g of titania, and kneading the binder-added mixture for one hour.

Figure 8A:
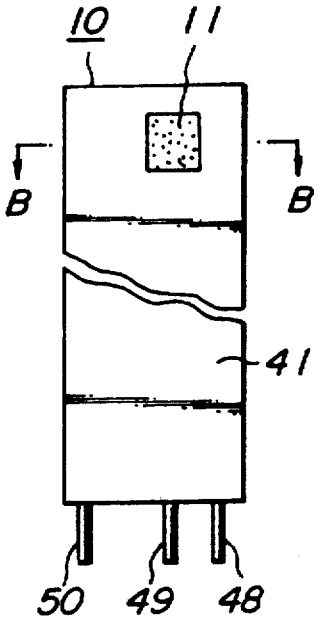
Figure 8B:
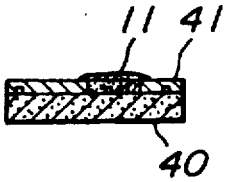

(5) Formation of a titania layer (II):

An outer titania layer (II) of the particle-addition method or the impregnation method was formed by spreading the corresponding paste, which paste was prepared in the above step (4), over the titania layer (I) as shown in FIG. 8A and FIG. 8B, drying the spread layer and baking the dried layer at 1,100° C. in an electric furnace for two hours.

Thus, samples of the titania thick film for the gas-sensitive element of the invention were produced.

The titania thick film formed by the above-mentioned steps (1) through (5) have different metallic catalyzer in the outer surface layer than that in the inner layer in the proximity of the electrodes. The kind and the amount of the metallic catalyzer can be arbitrarily controlled by selecting proper metal powder particles or proper solution of salt of metallic catalyzer. Besides, the grain size of the ceramic particles can be also arbitrarily controlled by regulating the calcining temperature. The thickness of the titania layer carrying the metallic catalyzer can be controlled by adjusting the amount of the paste to be spread.

The metallic catalyzer can be distributed by either of the impregnation method and the particle-addition method, and as long as the amount of the metallic catalyzer distributed is the same, the same catalytic effect is expected. For instance, the particle addition method may be used for the titania layer (I) while the impregnation method may be used for the titania layer (II).

Figure 9A:
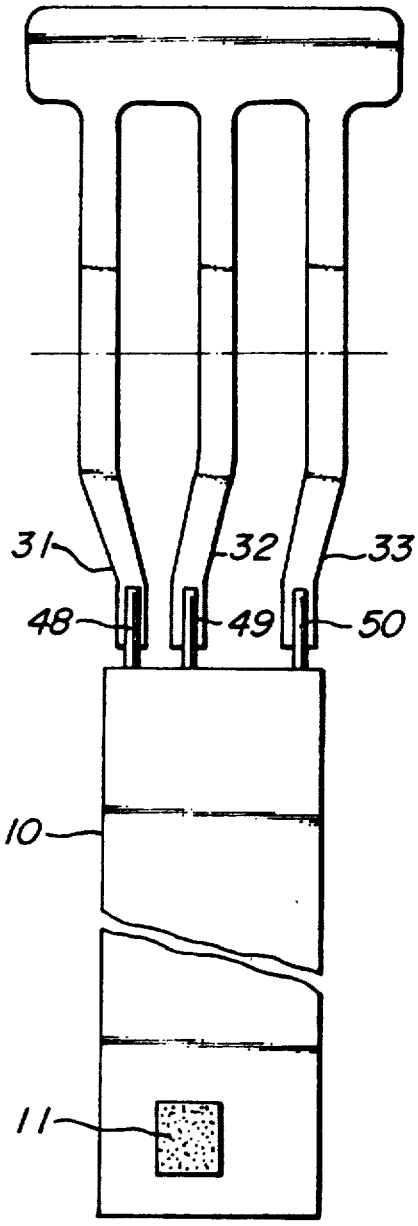
FIG. 9A is a schematic elevation, showing the manner in which lead wires of the gas-sensitive element are connected to terminals of the oxygen sensor.
Figure 9B:
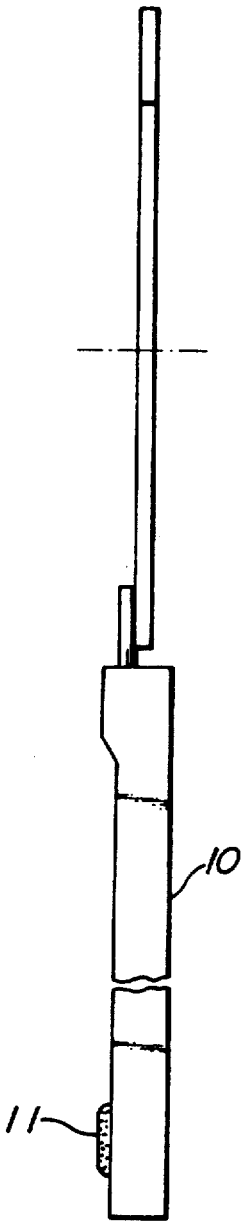
FIG. 9B is a side view, taken from the right-hand side of FIG. 9A.

The platinum lead wires 48 through 50 extending outwardly from the gas sensor 10 were connected to the terminals 31 through 33 respectively in a manner as shown in FIG. 9A. FIG. 9B shows a side view of the illustration of FIG. 9A.

Separately, the terminals 31 through 33 were made by etching a 0.5 mm thick nickel plate without severing them from each other as shown in FIG. 9A. The terminals 31 through 33 were brought in contact with the platinum lead wires 48 through 50 respectively, and the portions in contact with each other were bonded by spot welding. After the gas sensor 10 thus provided with the terminals was placed in the inner cylinder 14 carried by the body hardware 12 as shown in FIG. 2, the three terminals 31 through 33 were severed from each other at suitable portions so as to provide the terminals of certain lengths.

The three lead wires 21, 22 and 23 of FIG. 3 were then connected to the terminals 31, 32 and 33 by using the compressible connectors 24, 25 and 26, respectively. After the lead wires 21 through 23 and the sealing 20 were inserted in the outer cylinder 19 in position, the outer cylinder 19 is fitted on the body hardware 12 and welded thereto so as to complete the sensor as shown in FIG. 1.

Figure 10:
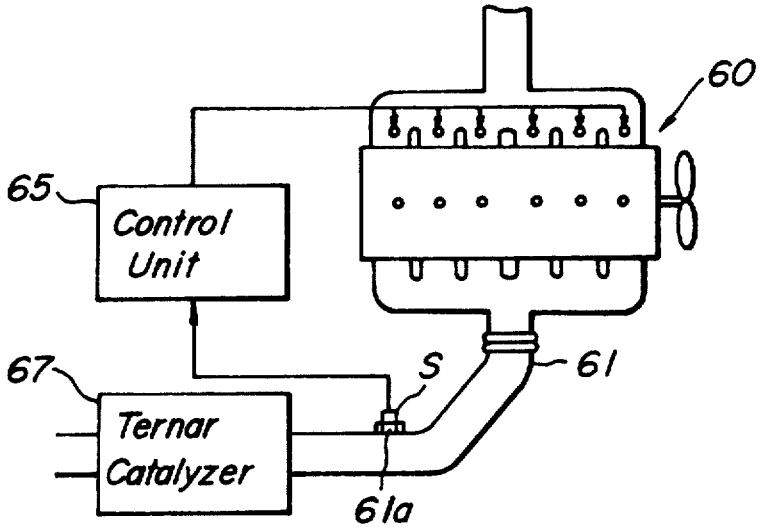
FIG. 10 is a schematic block diagram of a system for durability test of the oxygen sensor by using an internal combustion engine.

The sensor thus assembled was mounted on the exhaust pipe 61 of an EFI (electronic fuel injection) type test automobile engine 60 with a piston displacement of 21, which exhaust pipe 61 was connected to an exhaust gas cleaning system with a ternary catalyzer unit 67, as shown in FIG. 10. The engine 60 was run under the Hot Transient Mode of EPA (Environmental Protection Agency) of the U.S.A., and the emission during such run was measured by taking the exhaust gas by CVS (constant volume sampling) method.

Figure 11:
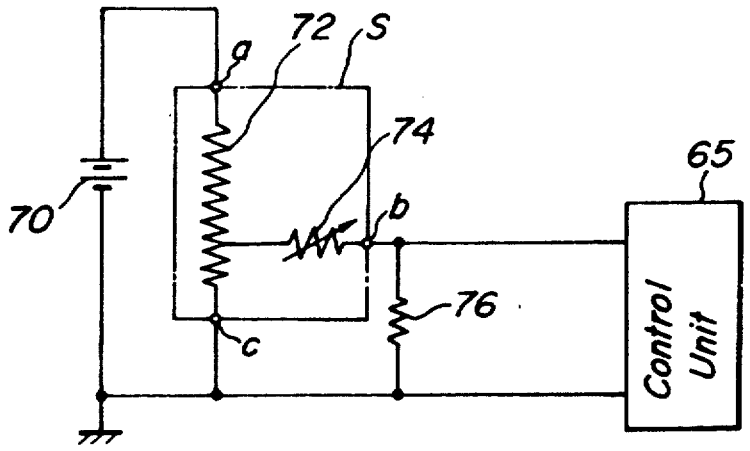
FIG. 11 is a circuit diagram of a control unit which is used in the durability test.

In FIG. 10, the symbol S represents an oxygen sensor, which may or may not be a product of the present invention. The sensor S is fixed to a sensor-mounting portion 61a of the exhaust pipe 61. A control unit 65 controls the engine exhaust gas system including the ternary catalyzer unit 67. FIG. 11 shows circuit diagram of the system connected to both a heater 72 and a variable resistance 74 representing the gas-sensitive element 11 of the sensor S. A. comparison resistance 76 is connected between the ground and one terminal of the variable resistance 74.

EXPERIMENT

Figure 12:
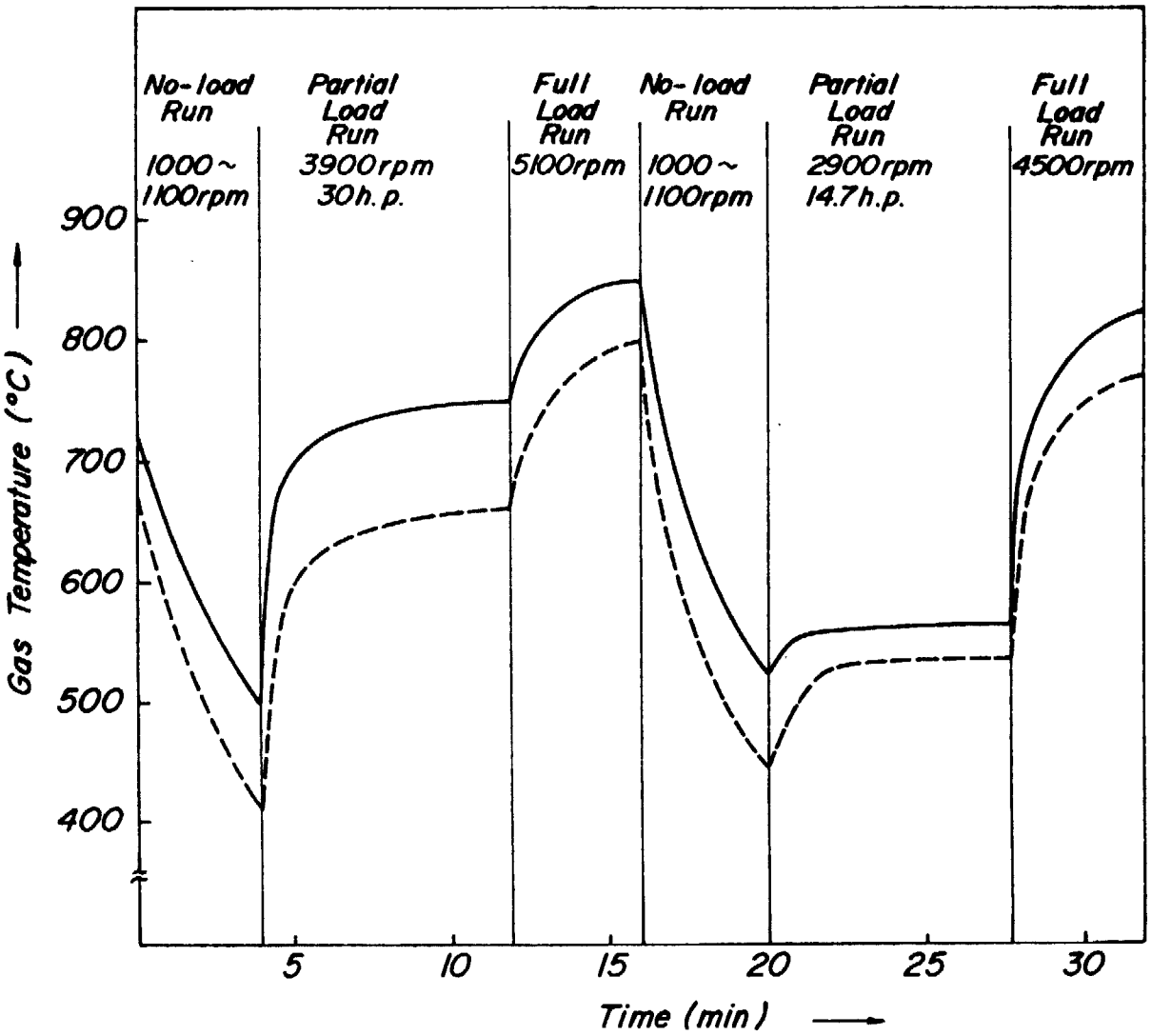
FIG. 12 is a graph showing the gas temperature change in the durability test.

Six samples of the gas-sensitive element of the invention were made in the manner as described above. Durability tests were carried out on the samples by using the system of FIG. 10 while running the test engine 60 in a durability test mode as shown in FIG. 12. The performance of each sample of the invention was evaluated by subjecting it to the durability test for 300 hours so as to cause certain deterioration therein, and measuring the controlled air-fuel-ratio point shift and the emission before and after the durability test. For comparison, the same test and measurements were effected on three reference samples of the conventional gas-sensitive element.

The result is shown in Table 1. As can be seen from Table 1, the conventional gas-sensitive elements had a large change in the emission of Nox before and after the durability test and their controlled point was shifted to lean side.

On the other hand, the sample of the gas-sensitive element of the invention showed only slight change in the emission before and after the durability test, and their performance proved to be stable. Thus, with the gas-sensitive element of the invention, a stable exhaust gas control system can be produced.

TABLE 1

| | Reference | | | Invention | | | | | |
|---|---|---|---|---|---|---|---|---|---|
| | Sample No. | | | | | | | | |
| Remark | 1 | 2 | 3 | 4 | 5 | 6 | 7 | 8 | 9 |
| I* | | | | | | | | | |
| Thickness (μm) | 150 | 150 | 150 | 150 | 150 | 100 | 150 | 50 | 50 |
| Calcining temperature (°C.) | 1200 | 1200 | 1200 | 1200 | 1150 | 1150 | 1150 | 1150 | 1150 |
| Ceramic grain size (μm) | 0.5-3 | 0.5-3 | 0.5-3 | 0.5-3 | 0.5-0.2 | 0.5-2.5 | 0.5-2.5 | 0.5-2.5 | 0.5-2.5 |
| Catalyzer amount (mole %) | Pt 10 | Pt 10 | Pt 10 | Pt 5 Rh 0.5 | Pt 5 Rh 1 | Pt 5 Rh 0.25 | Pt 5 Rh 0.5 | [Pt] *Rh* 0.5 [Rh] *Pd* 0.02 | Pt 10 Rh 0.5 |
| Catalyzer grain size (μm) | about 0.5 | about 0.5 | about 0.5 | about 0.5 | about 0.3 | 0.3 | 0.3 | 0.3 | 0.3 |
| II* | | | | | | | | | |
| Thickness (μm) | 100 | 100 | 100 | 100 | 100 | 150 | 100 | 200 | 200 |
| Calcining temperature (°C.) | 1200 | 1300 | 1300 | 1300 | 1400 | 1150 | 1150 | 1150 | 1150 |
| Ceramic grain size (μm) | 0.5-3 | 1.5-4 | 1.5-4 | 1.5-4 | 2.5-5 | 0.5-2.5 | 0.5-2.5 | 0.5-2.5 | 0.5-2.5 |
| Catalyzer amount (mole %) | Pt 10 | Pt 10 | Pt 5 | Pt 5 | Pt 7 | Pt 5 Rh [0.3] *0.03* | Pt 7 | Pt 10 | Pt 5 |
| Catalyzer grain size (μm) | about 0.5 | about 0.5 | about 1.0 | about 1.0 | about 1.2 | about 0.3 | about 0.3 | about 0.3 | about 0.3 |
| III* | | | | | | | | | |
| A** | | | | | | | | | |
| CO | 1.3 | 1.0 | 0.8 | 0.8 | 0.6 | 1.0 | 0.6 | 0.5 | 0.6 |
| NOx | 0.2 | 0.5 | 0.6 | 0.6 | 0.8 | 0.3 | 0.7 | 0.9 | 0.7 |
| 55 mile Hz | 1.6 | 1.8 | 2.0 | 1.9 | 2.3 | 1.8 | 2.1 | 2.2 | 2.1 |
| B** | | | | | | | | | |
| CO | 0.5 | 0.7 | 1.1 | 0.7 | 0.6 | 0.9 | 0.6 | 0.4 | 0.6 |
| NOx | 0.8 | 0.7 | 0.4 | 0.7 | 0.8 | 0.4 | 0.6 | 0.8 | 0.6 |
| 55 mile Hz | 2.2 | 2.3 | 2.0 | 2.0 | 2.3 | 2.0 | 2.2 | 2.4 | 2.1 |

*I Inner layer in the proximity of electrodes
II Outer surface layer
III Emission g/mile (EPA HOT TRANSIENT MODE)
**A New gas-sensitive element
B After durability test Two-layered structures of the gas-sensitive element of the invention has been described, but it is also possible to make it in three or more layered structure. Further, even when an insulating coating is provided on the outer surface layer, the stable performance of the gas-sensitive element of the invention will not be changed.

As described in detail in the foregoing, with a multi-layered thick-film gas-sensitive element according to the invention, deterioration of the element, especially that of the metallic catalyzer in the outer surface layer, is drastically reduced, and instability in control performance due to the deterioration of the metallic catalyzer is substantially eliminated.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A thick-film gas-sensitive element of a laminate structure, comprising a ceramic substrate having a pair of electrodes disposed on an upper surface thereof; and a laminate gas-sensitive thick film deposited on said ceramic substrate upper surface so as to extend across the ends of the pair of electrodes, said *laminate* gas-sensitive thick film [consisting of ceramic semiconductor and metallic catalyzer distributed in the ceramic semiconductor and said gas-sensitive thick film] having an inner [portion] *layer* adjacent said substrate upper surface and at least one outer surface layer disposed on said inner [portion] *layer*, *said inner layer of said gas-sensitive thick film consisting of ceramic semiconductor and a first metallic catalyzer distributed in the ceramic semiconductor, said first metallic catalyzer containing 0.2 to 3 mole % rhodium (Rh) based on the amount of ceramic semiconductor in said inner layer and being a member selected from the group consisting of Rh, mixtures and alloys of Rh and platinum (Pt), and mixtures and alloys of Rh and palladium (Pd); and said outer surface layer of the gas-sensitive thick film consisting of ceramic semiconductor and a second metallic catalyzer distributed in the ceramic semiconductor, said second metallic catalyzer containing less than 0.2 mole % Rh based on the amount of ceramic semiconductor in said outer surface layer and being a member selected from the group consisting of Rh, Pt, Pd and mixtures and alloys thereof.* [said outer surface layer of the gas-sensitive thick film containing a smaller amount of metallic catalyzer than said inner portion of the gas-sensitive thick film.]

[2. A thick-film gas-sensitive element as set forth in claim 1, wherein the metallic catalyzer in the outer surface layer of the gas-sensitive thick film contains less than 0.2 mole % of rhodium (Rh) based on amount of the ceramic semiconductor therein, while the metallic catalyzer in the inner portion of the gas-sensitive thick film contains 0.2–3 mole % of rhodium (Rh) on a similar basis.]

3. A thick-film gas-sensitive element as set forth in claim 1, wherein the *second* metallic catalyzer in the outer surface layer of the gas-sensitive thick film has a larger grain size than [that] *the first metallic catalyzer* in the inner [portion] *layer* of the gas-sensitive thick film in the proximity of the electrodes.

4. A thick-film gas-sensitive element as set forth in claim 1, wherein the ceramic semiconductor in the outer surface layer of the gas-sensitive thick film has a larger grain size than that in the inner [portion] *layer* of the gas-sensitive thick film in the proximity of the electrodes.

5. A thick-film gas-sensitive element as set forth in claim 1, wherein the *second* metallic catalyzer in the outer surface layer of the gas-sensitive thick film contains platinum (Pt) particles with a grain size of larger than 0.5 μm, while the *first* metallic catalyzer in the inner [portion] *layer* of the gas-sensitive thick film contains particles of metal [selected from the group consisting of rhodium (Rh) and compounds thereof at a concentration of 0.2–3 mole % based on amount of ceramic semiconductor therein,] *having a* grain size of [metal particles in the inner portion being] less than 0.5 μm.

6. A thick-film gas-sensitive element as set forth in claim 1, wherein the gas-sensitive thick film has a laminate structure formed of fired paste layers of ceramic semiconductor, different layers having different dispersions of metallic catalyzer produced by impregnation of different solutions of salt of metallic catalyzer in the fired paste layers followed by thermal cracking of the salt.

7. A thick-film gas-sensitive element as set forth in claim 1, wherein the gas-sensitive thick film has a laminate structure formed of fired paste layers of ceramic semiconductor, different layers having different dispersions of metallic catalyzer produced by different mixing of [metal] *metallic* catalyzer particles in different ceramic semiconductor pastes followed by laminate spreading and firing of the ceramic semiconductor pastes.

8. A thick-film gas-sensitive element as set forth in claim 1, wherein the gas-sensitive thick film has a laminate structure formed of fired paste layers of ceramic semiconductor, said fired paste layers including at least one layer having a dispersion of metallic catalyzer produced by impregnation of solution of salt of the metallic catalyzer in the fired paste layer followed by thermal cracking of the salt, said fired paste layers including at least one other layer having a different dispersion of metallic catalyzer produced by mixing of particles of the metallic catalyzer in ceramic semiconductor paste followed by laminate spreading and firing of the ceramic semiconductor paste.

9. A thick-film gas-sensitive element as set forth in claim 1, further comprising a layer of ceramic particles bonded to the upper surface of said ceramic substrate adjacent the ends of said electrodes, said ceramic particles being made of the same material as said ceramic substrate and said ceramic particles forming projections on said ceramic substrate and having recesses defined therebetween to provide a roughened surface portion on said ceramic substrate.

*10. A thick-film gas-sensitive element as set forth in claim 1, wherein the first metallic catalyzer is selected from the group consisting of Rh, RhPt and RhPd.*

*11. A thick-film gas-sensitive element as set forth in claim 1, wherein the second metallic catalyzer is selected from the group consisting of RhPt and Pt.*

* * * * *